United States Patent [19]

Yu et al.

[11] 4,141,977

[45] * Feb. 27, 1979

[54] TREATMENT OF PSORIASIS WITH 6-SUBSTITUTED NICOTINAMIDES, 2-SUBSTITUTED PYRAZINAMIDES AND CLOSELY RELATED COMPOUNDS

[76] Inventors: Ruey J. Yu, 4400 Dexter St., Philadelphia, Pa. 19128; Eugene J. Van Scott, 1138 Sewell La., Rydal, Pa. 19046

[*] Notice: The portion of the term of this patent subsequent to Jan. 10, 1995, has been disclaimed.

[21] Appl. No.: 715,131

[22] Filed: Aug. 17, 1976

Related U.S. Application Data

[63] Continuation-in-part of Ser. No. 601,411, Aug. 4, 1975, Pat. No. 4,067,975.

[51] Int. Cl.$^2$ ............... A61K 31/455; A61K 31/495
[52] U.S. Cl. ............................ 424/250; 424/266; 424/263; 546/286; 546/288; 546/298; 546/291; 546/305; 546/309; 546/310; 546/313; 546/316; 546/318; 546/315; 544/406; 544/407; 544/408; 544/409; 544/336
[58] Field of Search ............................. 424/250, 266

[56] References Cited

U.S. PATENT DOCUMENTS

| | | | |
|---|---|---|---|
| 2,199,839 | 5/1940 | Renshaw et al. | 424/266 X |
| 2,791,534 | 5/1957 | Schaaf et al. | 424/365 |
| 3,337,570 | 8/1967 | Sherlock et al. | 424/266 X |
| 3,415,835 | 12/1968 | Stempel et al. | 424/266 X |

OTHER PUBLICATIONS

Zackheim, Arch Dermatol, vol. 111, Jul. 1975, pp. 880–882.

*Primary Examiner*—Albert T. Meyers
*Assistant Examiner*—Vera C. Clarke
*Attorney, Agent, or Firm*—LeBlanc & Shur

[57] ABSTRACT

A treatment to alleviate the symptoms of psoriasis consisting of topical application of a cream, ointment or lotion containing, as the principal active ingredient, one or more 6-substituted nicotinamides and or 2-substituted pyrazinamides is disclosed. The therapeutic composition may include a single member of the above active ingredients present in a total amount of from 0.01 to 5 percent by weight of the total composition, or a plurality thereof present in a preferred concentration range of from 0.02 to 2 percent by weight of the total composition. Topical application of the therapeutic composition in a cream, ointment, or a water or alcohol solution has been found to achieve from substantial to complete remissions of psoriasis in humans.

21 Claims, No Drawings

TREATMENT OF PSORIASIS WITH 6-SUBSTITUTED NICOTINAMIDES, 2-SUBSTITUTED PYRAZINAMIDES AND CLOSELY RELATED COMPOUNDS

CROSS-REFERENCE TO RELATED APPLICATION

This application is a continuation-in-part of our earlier application, Ser. No. 601,411, filed Aug. 4, 1975, now U.S. Pat. No. 4,067,975.

BACKGROUND OF THE INVENTION

This invention relates to a treatment for psoriasis and specifically to a composition containing one or more compounds which have been found to be effective when topically applied, to improve and heal the skin lesions of psoriasis in humans.

Psoriasis is a chronic disease, and remains a disfiguring and disabling cutaneous impairment to millions of persons. Its etiology is completely unknown, and therefore prevention remains inconceivable. Therapy has necessarily been empiric, and has included the systemic use of antimitotic drugs such as methotrexate to induce remissions of the lesions. However, acute and chronic toxicity on tissues other than skin has discredited use of methotrexate. Therefore it is imperative that other means of therapy be found by external delivery of drugs so that toxicity is confined chiefly to the skin, or by the discovery of new drugs having nontoxic attributes.

In our prior patent application entitled TREATMENT OF PSORIASIS, Ser. No. 371,516, filed June 19, 1973, now U.S. Pat. No. 3,904,766, we described and claimed the use of mechlorethamine hydrochloride ointment in the treatment of psoriasis by topical application. We also described that in an oil base the compound formed a stable composition.

Prior to our above invention mechlorethamine hydrochloride, a nitrogen mustard, had been generally discounted as a treatment for psoriasis because, in effective dosages a high percentage of patients became sensitized. In addition, the compound proved to be highly unstable in an aqueous solution and rapidly degraded to what was considered an ineffective byproduct by those skilled in the art.

The treatment described in our above application, however, was necessarily proceeded by inducing an immunological tolerance so that the patient would not be susceptible to a delayed hypersensitive reaction. The procedure for inducing immune tolerance included weekly intravenous injections of 0.2 milligrams of mechlorethamine hydrochloride in an aqueous solution over at least a three week period prior to initiation of topical therapy.

In our prior patent application Ser. No. 455,665, filed March 28, 1974, now U.S. Pat. No. 3,920,840, we described and claimed our discovery that psoriatic conditions could be successfully treated by utilizing one of the degradation products of mechlorethamine hydrochloride, N-methyldiethanolamine, a compound which is not primarily either antimitotic nor allergic. This compound was found to be essentially nontoxic to both animals and humans when used as a topical agent in a therapeutic composition containing from 0.5 to 5 percent by weight thereof. The compound also caused no detectable signs of any irritation to human skin.

In our parent patent application entitled TREATMENT OF PSORIASIS WITH 6-AMINONICOTINAMIDE AND THIONICOTINAMIDE, Ser. No. 601,411, filed Aug. 4, 1975, we describe and claim the use of 6-aminonicotinamide and thionicotinamide in the treatment of psoriasis by topical application.

Although 6-aminonicotinamide showed no toxic signs when topically applied to the skin of humans or animals, this compound did exhibit various symptoms of toxicity in animals when administered systemically at a dose of 40 mg/kg. Another shortcoming with this compound in a topical treatment of psoriasis is its potential irritability to psoriatic skin. In patients having greater than 20% of their skin involved with psoriatic lesions 6-aminonicotinamide on topical application appeared to irritate the lesion and therefore exacerbate the disease. Thionicotinamide is a relatively nontoxic substance. However, its irritability to psoriatic skin is even greater than that of 6-aminonicotinamide.

SUMMARY OF THE INVENTION

It has now been discovered that psoriatic conditions may also be successfully treated with certain 6-substituted nicotinamides, 2-substituted pyrazinamides or closely related compounds, which are relatively nontoxic and nonirritating.

In accordance with the present invention, the chemical compounds which are incorporated in compositions for topical application to alleviate the symptoms of psoriasis are of the formula:

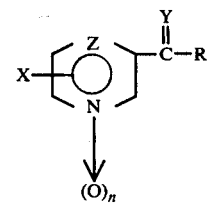

wherein
Z is CH or N,
n is 0 or 1,
X is hydroxyl, halogen, $CONH_2$, or $-N\ R_1R_2$, wherein $R_1$ and $R_2$ are independently hydrogen or alkyl of 1 to 6 carbon atoms, and $R_2$ may also be $NH_2$ or CHO,
Y is O or S,
R is H, OH, $NH_2$ or lower alkoxy of up to 6 carbon atoms, or else Y and R together are N, provided, however, that when X is $NH_2$, the 3-position substituent is other than carbamoyl, provided further, however, that when Z is CH, X is in the 6-position, and when Z is N, X is in the 2-position.

Preferably, the compounds of the class described by formula 1 are of the formula:

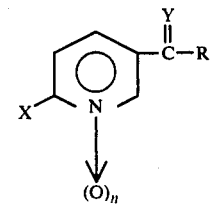

wherein X, Y, R and n are described hereinabove. More preferably, the compounds are of the formula:

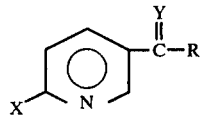

wherein X, Y and R are described hereinabove.

The psoriatic conditions may be successfully treated utilizing the compounds of the above formula, which are primarily neither antimitotic or allergenic. Therefore, it is unnecessary to induce immune tolerances prior to topical therapy with the compounds of the present invention. The present invention also includes the topical treatment of psoriatic lesions with one or more of the compounds of the above formula.

These compounds may be incorporated in therapeutic compositions as either free bases or as acid salts of HCl, $H_2SO_4$, $HNO_3$, or any other common acid, formed, for example, by dissolution of the free bases in a solution of the acid.

Preferred compounds which have been found to be particularly effective within the scope of the foregoing generic Formula (I) are listed below:

(1) 6-Aminonicotinic acid;
(2) 6-Aminonicotinic acid methyl ester;
(3) 6-Aminonicotinic acid ethyl ester;
(4) 6-Aminonicotinic acid tert-butyl ester;
(5) 6-Aminonicotinic acid nicotinic ester
(6) 6-Aminonicotinaldehyde
(7) 6-Hydroxynicotinic acid;
(8) 6-Methylaminonicotinamide;
(9) 6-Dimethylaminonicotinamide;
(10) 6-Formylaminonicotinamide;
(11) 6-Hydrazinonicotinamide;
(12) 6-Ethylaminonicotinamide;
(13) 6-Hydrazinonicotinic acid ethyl ester;
(14) 6-Chloronicotinamide;
(15) 6-Carbamoylnicotinamide;
(16) 6-Aminothionicotinamide;
(17) 6-Aminonicotinonitrile;
(18) 6-Aminonicotinamide-1-oxide;
(19) 2-Aminopyrazinamide;
(20) 2-Carbamoylpyrazinamide; and
(21) 6-Nicotinalaminonicotinamide.
(22) 6-Aminonicotinhydrazide It should be emphasized, however, that while the above compounds were found to be highly effective it was found that nicotinamide, nicotinic acid, isoniazid, and 2-aminonicotinic acid were totally ineffective in causing remissions of psoriatic conditions.

It has been established through extensive tests on humans having psoriasis that topical application of either an alcohol or water solution or an ointment or lotion containing from 0.01 to 5% of compounds of the above general formulae is effective in causing remissions of psoriatic conditions. Although these compounds were found to be effective when present in from 0.01 to 5 percent by weight of the total therapeutic composition, the preferred concentration range is from 0.02 to 2 percent thereof. The therapeutic compositions of this invention were found to be effective when applied on a daily basis, to cause within about 1-3 weeks time a return of the affected skin areas to a normal skin condition.

Accordingly, it is an object of this invention to provide a relatively nontoxic, nonallergenic medicinal composition which, when topically applied, will reliably alleviate the symptoms of psoriasis.

It is another object to provide a medicinal composition containing at least one 6-substituted nicotinamide, 6-substituted nicotinic acid and esters thereof, 2-substituted pyrazinamide and closely related compounds which, when topically applied, will alleviate the symptoms of psoriasis.

It is another object of this invention to provide a method for treating psoriasis with relatively nontoxic ointment or solution of water or alcohol containing 6-substituted nicotinamide, 2-substituted pyrazinamide or closely related compounds.

It is still another object to provide a safe and efficient method for treating the symptoms of psoriasis through regular topical application of a medicinal composition which will promote healing within about 1-3 weeks.

It is yet another object of this invention to provide a safe and efficient method for treating the symptoms of psoriasis through regular topical application of a medicinal composition containing from about 0.01 to 5 percent of at least one member selected from the group consisting of 6-substituted nicotinamides, 6-substituted nicotinic acid and esters thereof, 2-substituted pyrazinamides, 6-aminothionicotinamide and 6-aminonicotinamide-1-oxide.

Preparation of the Therapeutic Compositions

In order to prepare the compositions of this invention at least one of the aforementioned compounds is initially dissolved in a solvent such as water, ethanol, acetone or 1N HCl. The solution thus prepared may then be admixed in a conventional manner with commonly available ointment bases such as hydrophilic ointment, USP. The concentration of the compound ranges from 0.01 to 5.0 percent by weight of the total composition. The preferred concentration range, however, is from 0.01 to about 2 percent, more preferably from 0.02 to about 2 percent.

If desired, two or more of aforementioned compounds may be admixed as described above to form a composition of this invention. In this instance it is preferred that the concentration of the compounds not exceed about 2 percent by weight of the total composition.

The water, ethanol, acetone or HCl solvent used to initially dissolve the compound of this invention may have a concentration of from 1 to 20 percent by volume of the total composition. The preferred concentration thereof, however, is about 10 percent by volume of the total composition.

The therapeutic ointments of this invention, prepared as described above, may be stored in ointment jars at room temperature for extended periods of time. No change in clinical effectiveness due to prolonged periods of storage has been observed.

The compounds of this invention may also be utilized in a solution or lotion form. A typical solution utilizing the compounds of this invention comprises at least one of the above named compounds dissolved directly in a mixture of water, ethanol, and propylene glycol in a volume ratio of preferably 40:40:20, respectively. The ratio of each component, however, may vary, but the preferred concentrations of ethanol and propylene glycol should not exceed 70 percent and 30 percent, respectively. When solutions are formulated according to this invention the active compound concentration may also be from 0.01 to 5 percent by weight, but a concentration of from 0.1 to 2 percent is preferred. One or more compounds may be admixed in a solution of this invention, and it is preferred that the total concentration of the mixture not exceed about 2 percent by weight.

In an alternative way of preparing the therapeutic compositions, one of the aforementioned compounds of the present invention may also be directly incorporated into the composition without utilizing a solvent for dissolution.

EXAMPLES OF THE INVENTION

The following Examples are illustrative of formulations of compositions according to this invention. Although the Examples utilize a named compound, the Examples are not intended to be limited to the specific compound named, but any member of the above described group of compounds or combination thereof could be substituted therefor within the scope of this invention.

(A) Synthesis of 6-Aminonicotinamide-1-oxide

6-Aminonicotinamide, 50 g, was dissolved in warm glacial acetic acid, 500 ml. To this clear solution 30% hydrogen peroxide, 80 ml was slowly added with agitation. The mixture was then heated to 100° C. for 5 hours. The light brownish solution thus formed was evaporated to a syrupy residue which crystallized on cooling in an ice water bath. The crystals were washed with acetone and dried. The yield of practically pure 6-aminonicotinamide-1-oxide was 51.6 g. This product had a mobility (Rf) of 0.48 on thin-layer chromatogram using a solvent system of benzene:methanol, 1:1.

(B) Synthesis of 6-Formylaminonicotinamide

6-Aminonicotinamide, 5.6 g, was added to 90% formic acid, 15 ml. After all the crystals were dissolved, the clear solution was heated to 100° C. for 10 minutes. The mixture was cooled and then 4N NaOH was added to adjust the pH to 2.8. The white crystals which formed were separated by filtration and were washed once with cold water followed by acetone wash. The yield of 6-formylaminonicotinamide was 5.6 g. This product had Rf value of 0.53 on thin-layer chromatogram using a solvent system of benzene:methanol, 1:1.

(C) Synthesis of 6-Aminonicotinic acid

6-Aminonicotinamide, 200 g, was dissolved in warm 85% phosphoric acid, 700 ml. The clear solution was heated to 100° C. for 8 hours. The solution was then diluted with 1.5 Kg of ice water. The white crystals thus obtained were separated by filtration, and washed with ice water followed with an acetone wash. The yield of 6-aminonicotinic acid phosphoric salt was 310 g. This product in its phosphoric salt form may be directly incorporated into the therapeutic compositions of the present invention.

(D) Synthesis of 6-Aminonicotinic acid ethyl ester

6-Aminonicotinic acid, 40 g (or 6-aminonicotinic acid phosphoric salt, 62 g), was mixed with anhydrous ethanol 500 ml. The mixture was externally cooled by an ice water bath. Thionyl chloride, 50 ml, was slowly added into the mixture. (N,N-Dimethylformamide, 50 ml, may be added to dissolve any still undissolved phosphoric salt.) The reaction mixture was heated to 80° C. for 5 hours and was then evaporated to a syrupy reside which crystallized on addition of acetone. These crystals were separated by filtration and were redissolved in 400 g of ice water. 4N KOH was added to the solution to adjust the pH to 8. The white crystals thus formed were separated again by filtration and were washed with water. The yield of practically pure 6-aminonicotinic acid ethyl ester was 41.8 g. This product had an Rf value of 0.79 on thin-layer chromatogram using a solvent system of benzene:methanol, 1:1.

EXAMPLE 1

A 6-aminonicotinic acid 1 percent ointment is prepared as follows:

6-Aminonicotinic acid 1 g is dissolved in 7 ml of 1N HCl and 2 ml of water. The solution is admixed with USP grade hydrophilic ointment (90 g) to a uniform consistency. The ointment thus prepared is stored in opaque jars at room temperature.

EXAMPLE 2

A 6-aminonicotinic acid methyl ester 0.5 percent ointment may be prepared as follows:

6-Aminonicotinic acid methyl ester, 0.5 g, is dissolved in ethanol (12 ml) and the solution is admixed with USP grade hydrophilic ointment (90 g) to a uniform consistency. The ointment thus prepared is also stored in opaque jars at room temperature.

EXAMPLE 3

A 6-aminonicotinic acid ethyl ester 1 percent ointment may be prepared as follows:

6-Aminonicotinic acid ethyl ester, 1 g, is dissolved in 8 ml of ethanol and 4 ml of acetone and the solution is admixed with USP grade hydrophilic ointment (90 g) to a uniform consistency. The ointment thus prepared is also stored in opaque jars at room temperature.

EXAMPLE 4

A 6-formylaminonicotinamide 0.1 percent ointment may be prepared as follows:

6-Formylaminonicotinamide 0.1 g is dissolved in 5 ml of water and 4.9 ml of ethanol. The solution is admixed with hydrophilic ointment USP grade (90 g) to a uniform consistency. This ointment also may be stored in opaque jars at room temperature.

EXAMPLE 5

A 6-aminonicotinamide-1-oxide 0.5 percent ointment may be prepared as follows:

6-Aminonicotinamide-1-oxide, 0.5 g, is dissolved in 12 ml of ethanol and the solution is admixed with USP grade hydrophilic ointment (90 g) to a uniform consistency. The ointment thus prepared is also stored in opaque jars at room temperature.

EXAMPLE 6

A 6-aminothionicotinamide 0.5 percent ointment may be prepared as follows:

6-Aminothionicotinamide, yellowish crystals, 0.5 g is dissolved in 12 ml of ethanol and the solution is admixed with USP grade hydrophilic ointment (90 g) to uniform consistency. This ointment also may be stored in opaque jars at room temperature.

EXAMPLE 7

A 6-aminonicotinonitrile 1 percent ointment may be prepared as follows:

6-Aminonicotinonitrile, 1 g, is dissolved in 15 ml of acetone and the solution is admixed with USP grade hydrophilic ointment (87 g) to a uniform consistency. The ointment thus prepared is also stored in opaque jars at room temperature.

EXAMPLE 8

A 2-carbamoylpyrazinamide 1 percent ointment is prepared as follows:

2-Carbamoylpyrazinamide, also known as 2,3-pyrazinedicarboxamide, 1 g, is dissolved in 5 ml of acetone. The solution is admixed with USP grade hydrophilic ointment (90 g) to a uniform consistency. The ointment also may be stored in opaque jars at room temperature.

EXAMPLE 9

A 6-aminomicotinic acid ethyl ester 0.2 percent lotion is prepared as follows:

6-Aminonicotinic acid ethyl ester 0.2 g is dissolved in 6 ml of ethanol and the solution is admixed with 95 g of a water-in-oil lotion prepared from mineral oil, cottonseed oil, isopropyl palmitate and water with a surfactant such as sorbitan sesquioleate. The ingredients in said water-in-oil lotion are present for example in 10:10:5:70:5 parts by weight respectively. The lotion thus prepared is stored in a plastic squeeze bottle having a nozzle attached thereto. The lotion is suitable for use in an area such as the scalp.

EXAMPLE 10

A formulation without using any solvent for dissolution may be prepared as follows:

6-Aminonicotinamide-1-oxide powder, 1 g is directly admixed with 99 g of water-in-oil ointment prepared from mineral oil, petrolatum, spermaceti and water with a surfactant such as sorbitan sesquioleate. The ingredients of said water-in-oil ointment are present in 10:10:6:68:6 parts by weight, respectively. The ointment thus prepared is stored in opaque jars at room temperature.

EXAMPLE 11

A 6-aminonicotinic acid methyl ester 1 percent ointment may be prepared as follows:

6-Aminonicotinic acid methyl ester, 1 g, is dissolved in anhydrous ethanol (9 ml) and the solution is admixed with white petrolatum USP grade (54 g) and liquid petrolatum USP grade (36 g) to a uniform consistency. This ointment also may be stored in opaque jars at room temperature.

EXAMPLE 12

A 6-aminonicotinaldehyde 1 percent ointment is prepared as follows:

6-Aminonicotinaldehyde 1 g is dissolved in 10 ml of ethanol. The solution is admixed with USP grade hydrophilic ointment (90 g) to a uniform consistency. The ointment thus prepared is also stored in opaque jars at room temperature.

TEST RESULTS

In order to evaluate the compounds of this invention a total of more than 30 patients having psoriasis were treated with the composition as follows:

Patients with psoriasis were instructed to apply a thin film of an ointment or lotion formulated according to the above Examples to circumscribed areas of lesions. Twice daily topical application was continued for several weeks. Generally, the affected skin became less scaly and less erythematous after one week of topical treatment. The scaly and erythematous lesions ordinarily were substantially restored to normal appearing skin after two weeks of treatment. The sites of the lesions, devoid of any scales and erythema, usually reached an improved state comparable to normal skin within two or three weeks after initial treatment.

Once normal appearing skin was restored it remained improved for several weeks up to several months, varying from patient to patient, without further application of the ointment. It is, however, necessary to continue the application of the ointment in order to maintain the skin free from recurrence of the overt disease.

In each of the tests, the compositions utilized were formulated according to the above representative Examples and contained compounds of this invention present in a total concentration of from 0.2 to 1 percent, by weight.

|  | Compound | Number of Patients | Therapeutic Effectiveness |
|---|---|---|---|
| 1. | 6-Aminonicotinic Acid | 4 | 4+ |
| 2. | 6-Aminonicotinic Acid Methyl Ester | 20 | 4+ |
| 3. | 6-Aminonicotinic Acid Ethyl Ester | 20 | 4+ |
| 4. | 6-Aminonicotinic acid tert-butyl ester | 2 | 4+ |
| 5. | 6-Aminonicotinic acid nicotinic ester | 2 | 4+ |
| 6. | 6-Aminonicotinaldehyde | 2 | 4+ |
| 7. | 6-Hydroxynicotinic Acid | 3 | 4+ |
| 8. | 6-Methylaminonicotinamide | 2 | 3+ |
| 9. | 6-Dimethylaminonicotinamide | 3 | 3+ |
| 10. | 6-Formylaminonicotinamide | 3 | 4+ |
| 11. | 6-Hydrazinonicotinamide | 2 | 3+ |
| 12. | 6-Ethylaminonicotinamide | 2 | 3+ |
| 13. | 6-Hydrazinonicotinic Acid Ethyl Ester | 2 | 3+ |
| 14. | 6-Chloronicotinamide | 2 | 3+ |
| 15. | 6-Carbamoylnicotinamide | 2 | 4+ |
| 16. | 6-Aminothionicotinamide | 3 | 3+ |
| 17. | 6-Aminonicotinonitrile | 3 | 3+ |
| 18. | 6-Aminonicotinamide-1-oxide | 10 | 4+ |
| 19. | 2-Aminopyrazinamide | 2 | 4+ |
| 20. | 2-carbamoylpyrazinamide | 4 | 4+ |
| 21. | 6-Nicontinalaminonicotinamide | 2 | 4+ |
| 22. | 6-Aminonicotinhydrazide | 3 | 3+ |

3+: Disappearance of scale from lesions.
4+: Restoration to normal looking skin.

As shown by the above Table, 13 compounds achieved a 4+ result, restoring normal looking skin in all patients tested. The rest of the compounds achieved at least a 3+ result and achieved a restoration of normal textured skin in that the lesions were still only erythematous. The method of application utilized herein generally required twice daily topical applications, and the scaly lesions ordinarily were substantially cleared after two weeks of treatment.

As noted above, use of the compositions of this invention, however, do not result in a permanent cure. It has been observed that when regular application of a composition of this invention is terminated, normal appearing skin will remain for varying periods of time from a few weeks to several months depending upon the patient. However, when regular applications are resumed the lesions again disappear and normal appearing skin is restored.

In summary, this invention includes the discovery of relatively nontoxic compositions which are neither antimitotic nor allergic and which are useful for alleviating the symptoms of psoriasis. The compositions may either be an ointment, a cream, a lotion or a water or alcohol solution of one or more of the above-described 6-substituted nicotinamides and 1-oxides thereof, 6-substituted nicotinic acids and esters thereof, and 2-substituted pyrazinamides. Specifically, the most active compounds of this invention are represented by 6-aminonicotinic acid, 6-aminonicotinic acid methyl ester, 6-aminonicotinamide-1-oxide, 6-hydroxynicotinic acid, 6-carbamoylnicotinamide, 2-aminopyrazinamide and 2-carbamoylpyrazinamide. One or more of these compounds is present in the vehicle, either ointment, cream, lotion or water or alcohol solution, in a total concentration of from 0.01 to 5 percent by weight.

This invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method for alleviating the symptoms of psoriasis in humans suffering therefrom comprising:
 applying, topically, to involved areas of the human body an effective amount of a composition containing at least one member selected from the group consisting of:

(1) 6-Aminonicotinic acid;
(2) 6-Aminonicotinic acid methyl ester;
(3) 6-Aminonicotinic acid ethyl ester;
(4) 6-Aminonicotinic acid tert-butyl ester;
(5) 6-Aminonicotinic acid nicotinic ester;
(6) 6-Aminonicotinaldehyde;
(7) 6-Hydroxynicotinic acid;
(8) 6-Methylaminonicotinamide;
(9) 6-Dimethylaminonicotinamide;
(10) 6-Formylaminonicotinamide;
(11) 6-Hydrazinonicotinamide;
(12) 6-Ethylaminonicotinamide;
(13) 6-Hydrazinonicotinic acid ethyl ester;
(14) 6-Chloronicotinamide;
(15) 6-Carbamoylnicotinamide;
(16) 6-Aminothionicotinamide;
(17) 6-Aminonicotinonitrile;
(18) 6-Aminonicotinamide-1-oxide;
(19) 2-Aminopyrazinamide;
(20) 2-Carbamoylpyrazinamide;
(21) 6-Nicotinalaminonicotinamide; and
(22) 6-Aminonicotinhydrazide
 in a concentration from about 0.01 to 5% by weight of the total composition, in a pharmaceutically acceptable carrier.

2. The method of claim 1, wherein said carrier comprises a solvent selected from the group consisting of water, ethanol, acetone, and 1N HCl.

3. The method of claim 1, wherein said carrier comprises a hydrophilic ointment.

4. A therapeutic composition for alleviating the symptoms of psoriasis by topical application thereof to the involved areas of the human body, said composition comprising:
 6-aminonicotinic acid nicotinic ester
 in a concentration of from about 0.01 to 5% by weight of the total composition in a pharmaceutically acceptable carrier.

5. A therapeutic composition for alleviating the symptoms of psoriasis by topical application thereof to the involved areas of the human body, said composition comprising:
 6-Aminonicotinaldehyde
 in a concentration of from about 0.01 to 5% by weight of the total composition in a pharmaceutically acceptable carrier.

6. A therapeutic composition for alleviating the symptoms of psoriasis by topical application thereof to the involved areas of the human body, said composition comprising:
 6-Hydroxynicotinic acid
 in a concentration of from about 0.01 to 5% by weight of the total composition in a pharmaceutically acceptable carrier.

7. A therapeutic composition for alleviating the symptoms of psoriasis by topical application thereof to the involved areas of the human body, said composition comprising:
 6-Methylaminonicotinamide
 in a concentration of from about 0.01 to 5% by weight of the total composition in a pharmaceutically acceptable carrier.

8. A therapeutic composition for alleviating the symptoms of psoriasis by topical application thereof to the involved areas of the human body, said composition comprising:
 6-Dimethylaminonicotinamide
 in a concentration of from about 0.01 to 5% by weight of the total composition in a pharmaceutically acceptable carrier.

9. A therapeutic composition for alleviating the symptoms of psoriasis by topical application thereof to the involved areas of the human body, said composition comprising:
 6-Formylaminonicotinamide
 in a concentration of from about 0.01 to 5% by weight of the total composition in a pharmaceutically acceptable carrier.

10. A therapeutic composition for alleviating the symptoms of psoriasis by topical application thereof to the involved areas of the human body, said composition comprising:
 6-Hydrazinonicotinamide
 in a concentration of from about 0.01 to 5% by weight of the total composition in a pharmaceutically acceptable carrier.

11. A therapeutic composition for alleviating the symptoms of psoriasis by topical application thereof to the involved areas of the human body, said composition comprising:
 6-Ethylaminonicotinamide
 in a concentration of from about 0.01 to 5% by weight of the total composition in a pharmaceutically acceptable carrier.

12. A therapeutic composition for alleviating the symptoms of psoriasis by topical application thereof to the involved areas of the human body, said composition comprising:
 6-Hydrazinonicotinic acid ethyl ester
 in a concentration of from about 0.01 to 5% by weight of the total composition in a pharmaceutically acceptable carrier.

13. A therapeutic composition for alleviating the symptoms of psoriasis by topical application thereof to the involved areas of the human body, said composition comprising:
 6-Chloronicotinamide
 in a concentration of from about 0.01 to 5% by weight of the total composition in a pharmaceutically acceptable carrier.

14. A therapeutic composition for alleviating the symptoms of psoriasis by topical application thereof to the involved areas of the human body, said composition comprising:

6-Carbamoylnicotinamide in a concentration of from about 0.01 to 5% by weight of the total composition in a pharmaceutically acceptable carrier.

15. A therapeutic composition for alleviating the symptoms of psoriasis by topical application thereof to the involved areas of the human body, said composition comprising:

6-Aminothionicotinamide in a concentration of from about 0.01 to 5% by weight of the total composition in a pharmaceutically acceptable carrier.

16. A therapeutic composition for alleviating the symptoms of psoriasis by topical application thereof to the involved areas of the human body, said composition comprising:

6-Aminonicotinonitrile in a concentration of from about 0.01 to 5% by weight of the total composition in a pharmaceutically acceptable carrier.

17. A therapeutic composition for alleviating the symptoms of psoriasis by topical application thereof to the involved areas of the human body, said composition comprising:

6-Aminonicotinamide-1-oxide in a concentration of from about 0.01 to 5% by weight of the total composition in a pharmaceutically acceptable carrier.

18. A therapeutic composition for alleviating the symptoms of psoriasis by topical application thereof to the involved areas of the human body, said composition comprising:

2-Aminopyrazinamide in a concentration of from about 0.01 to 5% by weight of the total composition in a pharmaceutically acceptable carrier.

19. A therapeutic composition for alleviating the symptoms of psoriasis by topical application thereof to the involved areas of the human body, said composition comprising:

2-Carbamoylpyrazinamide in a concentration of from about 0.01 to 5% by weight of the total composition in a pharmaceutically acceptable carrier.

20. A therapeutic composition for alleviating the symptoms of psoriasis by topical application thereof to the involved areas of the human body, said composition comprising:

6-Nicotinalaminonicotinamide in a concentration of from about 0.01 to 5% by weight of the total composition in a pharmaceutically acceptable carrier.

21. A therapeutic composition for alleviating the symptoms of psoriasis by topical application thereof to the involved areas of the human body, said composition comprising:

6-Aminonicotinhydrazide in a concentration of from about 0.01 to 5% by weight of the total composition in a pharmaceutically acceptable carrier.

* * * * *

UNITED STATES PATENT OFFICE
CERTIFICATE OF CORRECTION

Patent No. 4,141,977      Dated February 27, 1979

Inventor(s) Yu et al

It is certified that error appears in the above-identified patent and that said Letters Patent are hereby corrected as shown below:

Column 1, line 68, correct the spacing between the words "MENT OF PSORIASIS WITH 6-".

Column 4, line 60, change "compirses" to --comprises--.

Column 5, line 67, change "reside" to --residue--.

Column 7, line 16, change "6-aminomicotinic" to --6-aminonicotinic--.

Signed and Sealed this

Eighth Day of January 1980

[SEAL]

Attest:

Attesting Officer

SIDNEY A. DIAMOND

Commissioner of Patents and Trademarks